United States Patent
McCleskey et al.

(10) Patent No.: US 7,129,093 B2
(45) Date of Patent: Oct. 31, 2006

(54) QUANTITATIVE METHOD OF DETERMINING BERYLLIUM OR A COMPOUND THEREOF IN A SAMPLE

(75) Inventors: T. Mark McCleskey, Los Alamos, NM (US); Deborah S. Ehler, Los Alamos, NM (US); Kevin D. John, Santa Fe, NM (US); Anthony K. Burrell, Los Alamos, NM (US); Gavin E. Collis, Los Alamos, NM (US); Edel M. Minogue, Los Alamos, NM (US); Benjamin P. Warner, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 10/812,444

(22) Filed: Mar. 30, 2004

(65) Prior Publication Data
US 2005/0221498 A1    Oct. 6, 2005

(51) Int. Cl.
*G01N 33/20* (2006.01)
(52) U.S. Cl. .............. 436/79; 252/301.26; 436/73; 436/172; 436/175; 436/181; 546/101; 546/110
(58) Field of Classification Search .......... 422/68.1, 422/82.05, 82.08; 436/73, 79, 172, 175, 436/181; 252/301.26; 546/1, 26, 79, 101, 546/110
See application file for complete search history.

(56) References Cited

U.S. PATENT DOCUMENTS 3,488,238 A * 1/1970 Batiuk et al. ............... 216/101

OTHER PUBLICATIONS

Sill, C. W. et al, Analytical Chemistry 1959, 598-608.*
McVay, T. N., Bureau of Mines Report of Investigations 1960, No. 5620, 10 pages.*
Patten, L. E. et al, U.S. Geological Survey Professional Paper 1962, No. 450-C, 103-104.*
Missel, L. et al, Metal Finishing 1965, 63, 69-71.*
Petidier, A. et al, Talanta 1985, 32, 1041-1045.*
Salinas, F. et al, Analyst 1987, 112, 645-648.*
Jalkanen, L. M. et al, Journal of Analytical Atomic Spectrometry 1996, 11, 365-369.*
Matsumiya, H. et al, Analyst 2001, 126, 2082-2086.*
Schneider, W. et al, Archiv der Pharmazie 1961, 294, 645-654.*
Martens, R. J. et al, Tetrahedron Letters 1962, 643-645.*
Chaudhuri, N. K. et al, Analytica Chimica Acta 1971, 57, 193-199.*
McManus, S. P. et al, Tetrahedron Letters 1985, 26, 4571-4574.*
Medvedev, A. S. et al, Izvestiya Vysshikh Uchebnykh Zavedenii, Tsvetnaya Metallurgiya 1991, 64-68.*
Karichiappan, K. et al, Australian Journal of Chemistry 2000, 53, 743-747.*

* cited by examiner

*Primary Examiner*—Arlen Soderquist
(74) *Attorney, Agent, or Firm*—Bruce H. Cottrell

(57) ABSTRACT

A method of determining beryllium or a beryllium compound thereof in a sample, includes providing a sample suspected of comprising beryllium or a compound thereof, extracting beryllium or a compound thereof from the sample by dissolving in a solution, adding a fluorescent indicator to the solution to thereby bind any beryllium or a compound thereof to the fluorescent indicator, and determining the presence or amount of any beryllium or a compound thereof in the sample by measuring fluorescence.

13 Claims, 2 Drawing Sheets

QUANTITATIVE METHOD OF DETERMINING BERYLLIUM OR A COMPOUND THEREOF IN A SAMPLE

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates to the detection and quantification of beryllium by fluorescence. More particularly, the present invention relates to the detection and quantification of beryllium at low levels and in the presence of other metals by fluorescence.

BACKGROUND OF THE INVENTION

Beryllium is a toxic metal that is used in a wide variety of industries including electronics, aerospace, and the DOE complex. Exposure to beryllium containing particles can lead to a lung disease called chronic beryllium disease (CBD). CBD involves an uncontrolled immune response in the lungs that can lead to deterioration in breathing capacity and ultimately death. It is clear that even in processes where beryllium dust has been controlled to very low levels cases of disease still persist. In fact, there have been cases of CBD reported in people that have had no obvious direct contact with beryllium operations. Despite the fact that very low exposure levels can lead to CBD, the onset of disease can take decades. Over 150 people from one facility alone have been diagnosed with CBD.

Recent new regulations dictate a permissible exposure limit of 2.0 $\mu g/m^3$, a housekeeping level of 3 $\mu g/100\ cm^2$ on a surface, and a release level for materials of 0.2 $\mu g/100\ cm^2$. Currently, thousands of swipes are analyzed annually for beryllium. In addition OSHA has detected airborne levels of beryllium at numerous companies within the United States. The present technique is to swipe an area with a filter paper or pull a known volume of air through a filter paper, do a microwave digestion with acid, and then analyze by inductively coupled plasma atomic emission. This process can take two days or more and is not readily fieldable. The inductively coupled plasma (ICP) atomic emission technique also requires the entire sample in order to meet the detection levels so that a sample that came up positive for beryllium can never be checked or verified with a second run.

Although there are several reports of being able to detect beryllium with a fluorescent indicator, there are no fluorimetric beryllium detection methods that have been approved for use by governmental concerns. Three key elements to a useful detection system have been missing previously. First, the detection system must be capable of dissolving beryllium oxide and beryllium metal. Second, the detection system must work in the presence of other metals and fluoride. Third, the detection system must be easy to use and preferably offer the ability to be field portable. Most fluorescent indicators reported in literature do not tolerate the presence of fluoride, which is critical if a fluoride-based medium is used to dissolve the beryllium. The few reports of fluorescent indicators that can tolerate fluoride, have used complicated procedures involving heating with acid for dissolution and a titration process to obtain the final pH that require long periods of time and prohibit use in the field.

The extensive chemistry required in previous fluorescent systems and the interferences from other metals has limited their use, and to date there is no simple approach to beryllium detection by fluorescence. A quick, simple approach has now been developed for the detection and quantification of beryllium.

It is an object of the present invention to provide a quantitative method of determining beryllium or a compound thereof (including beryllium oxide) in a sample, which has a fast turnaround time and can be made to be readily field portable.

Another object of the present invention is to provide a quantitative method of determining beryllium or a compound thereof in a sample, which can tolerate a wide variety of metals, including iron, aluminum, and/or uranium at high levels as well as high concentrations of fluoride without affecting the detection of beryllium or a compound thereof.

Another object of this invention is to provide a synthetic route to making 10-hydroxybenzo[h]quinoline-7-sulfonate, the preferred indicator used to detect beryllium.

SUMMARY OF THE INVENTION

In accordance with the purposes of the present invention, as embodied and broadly described herein, the present invention provides a method of determining the presence and amount of beryllium or a beryllium compound in a sample including admixing a sample suspected of containing beryllium or a beryllium compound with a dissolution solution for sufficient time whereby beryllium or a beryllium compound within said sample is dissolved, mixing a portion from the admixture with a buffered solution containing a fluorescent indicator capable of binding beryllium or a beryllium compound to the fluorescent indicator, and, determining the presence or amount of beryllium or a beryllium compound within the sample by measuring fluorescence from the fluorescent indicator.

The present invention further provides a composition of matter including an aqueous solution containing 10-hydroxybenzo[h]quinoline-7-sulfonate and a buffer with a $pK_a$ between 7 and 13.5. In one embodiment, the composition of matter further includes a metal chelating agent such as EDTA and the like.

The present invention further provides a composition of matter of the chemical formula $C_9H_5NBrOR_1$ with the structure

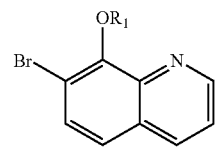

wherein $R_1$ is selected from the group consisting of tosylate $(CH_3C_6H_4)$ or triflate $(CF_3SO_2)$.

The present invention still further provides a composition of matter of the structure

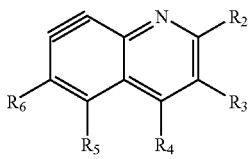

wherein $R_2$, $R_3$, $R_4$, $R_5$, $R_6$ are each independently selected from the group consisting of hydrogen, an alkyl group having from 1–5 carbons, an aryl group, an alkyl-substituted aryl group having from 1–10 carbons, nitro, an alkoxy group having from 1–10 carbons, a substituted aryl group having nitro substitution, a substituted aryl group having carboxylic acid substitution, a substituted aryl group having phosphoric acid substitution, and a substituted aryl group having azo substitution.

The present invention still further provides a composition of matter of the chemical formula $C_{13}H_8NOR_{12}$ with the structure

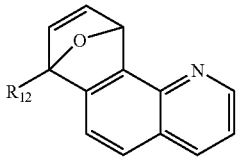

wherein $R_{12}$ is selected from the group consisting of hydrogen, $SiMe_3$, an alkyl group having from 1–5 carbons, an aryl, an alkyl-substituted aryl group having from 1–10 carbons, $N(R_{13})_2$, $O(R_{14})$, $C(OR_{15})_2$, $S(R_{16})$, or $Sn(R_{17})_3$ where $R_{13}$, $R_{14}$, $R_{15}$, $R_{16}$ and $R_{17}$ are each independently selected from an alkyl group have from 1–5 carbons, an aryl group, an alkyl-substituted aryl group having from 1–10 carbons.

DETAILED DESCRIPTION

Figure 1:
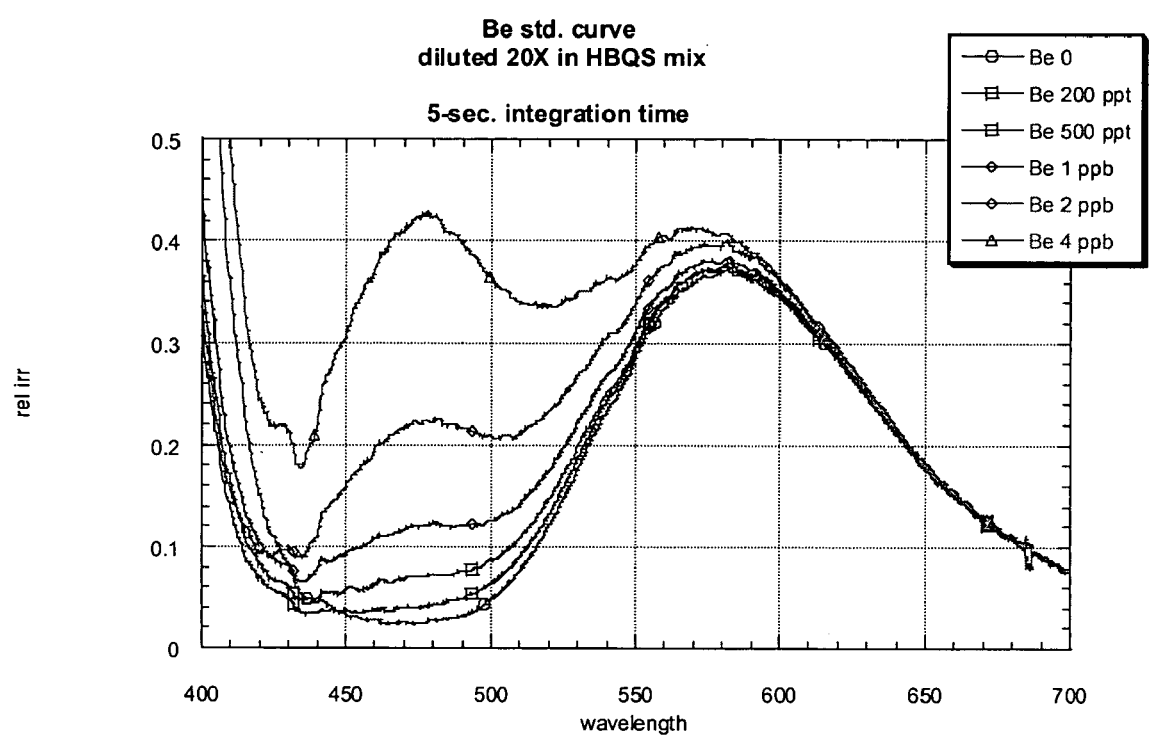
FIG. 1 shows a graph plotting the fluorescence curve resulting from various beryllium concentrations in accordance with the process of the present invention.

The present invention is concerned with a process of determining the presence and amount of beryllium or a beryllium compound in a sample. The advantages of the process of the present invention include: a simple dissolution step that can dissolve beryllium oxide and beryllium metal in less than thirty minutes by agitation; tolerance of a wide variety of other metals and fluoride at large concentrations; the use of a final buffered solution to avoid titration, a fast turnaround time of less than one hour and the ability to be field portable. In a preferred embodiment of the invention, the dissolution technique involves use of ammonium bifluoride. In another preferred embodiment of the invention, a buffered solution including the fluorescent indicator is used and is essential to fast detection that can be done in the field.

As a preferred fluorescent indicator, 10-hydroxybenzo[h]quinoline-7-sulfonate, is a material that is not commercially available, a synthetic route is also provided. The buffered solution preferably includes a buffer having a pKa between about 7 and 13.5. More preferably, the buffer is an amine buffer and most preferably is an amino acid such as lysine.

The present invention is also concerned with selected intermediates developed in the synthetic route of forming 10-hydroxybenzo[h]quinoline-7-sulfonate.

The method of the present invention involves obtaining a sample (such as by swiping a surface) and then placing the sample into a vial and adding 5 mL of an ammonium bifluoride solution for dissolution. A 1 percent ammonium bifluoride solution can dissolve up to 10 mg of either beryllium or beryllium oxide in less than 30 minutes with simple shaking by hand for 5 minutes. Next, a 0.1 mL of the ammonium bifluoride solution (with dissolved sample) is added to 1.9 mL of a buffered indicator solution, containing a fluorescent indicator and a buffer, to neutralize the solution and bind beryllium or its oxide to the fluorescent indicator. The solution may also contain aminocarboxylates such as ethylenediaminetetraaceticacid (EDTA), diethylenetriaminetetraacetic acid (DTPA), triethylenetetraminehexaacetic acid (TTHA), and the like, or salts thereof, as a chelating agent to bind metals other than beryllium. Other chelating agents such as aminophosphonates may be used as well. There are a few preferable choices of indicators, all of which are based on forming six-member rings with the beryllium (or its oxide) bound to a phenolate oxygen and a pyridine nitrogen. The preferred indicator is 10-HBQS. When 10-HBQS is used as the fluorescent indicator, fluorescence at 475 nm can be used to quantitatively determine the beryllium (or its oxide) concentration from 10 nM to 10,000 nM and could readily be adjusted to other levels. Currently, this method determines between 0.004 μg and 4 μg per swipe. The most remarkable aspect of this method is its ability to tolerate a wide range of potentially interfering metals at high concentrations. A wide variety of metals including iron, aluminum, and uranium at levels 10,000 times the beryllium concentration have been tested and have seen no interference in detecting the beryllium.

The advantages of fluorescence include a fast turnaround time, the case of fielding a portable field device, and the ability to verify a result by rerunning fluorescence or doing inductively coupled plasma atomic emission on the 4.9 mL of the dissolution solution that remains unused. There are several commercial, portable fluorimeters that could be used in the field. The present method from dissolution to detection could be made field portable, has a low detection limit, and can tolerate a wide variety of interferences. The method has the potential to save both man-hours and costs for the tremendous amount of beryllium analysis that is currently being done.

The preferred indicator 10-HBQS is not commercially available, so as part of this invention we developed a new high yielding synthesis that provides functionality at the position para to the phenolic group as shown in Scheme 1. The success of this approach is dependant on two key processes; the generation and trapping of arynes with dienes in cycloadditions (step E) and the ethereal bridge ring opening of 7-oxabicyclo[2.2.1]heptane systems (step F). Reaction of the heteroaryne, 7,8-didehydroquinoline (7,8-quinolyne, compound (5)), with furan dienes affords endoxide adducts that have the required benz[h]quinoline ring system and functionality at the desired 7-position. The ring opening occurs in a regio-selective manner to provide either 10-HBQ or 10-HBQS depending on the initial diene used.

The preferred fluorescent indicator in the present invention is 10-hydroxybenzo[h]quinoline-7-sulfonate (10-HBQS). Although the presursor 10-hydroxybenzo[h]quinoline (10-HBQ) has been reported in many papers, a comprehensive search of the literature revealed only Schenkel-Rudinö et al., Helv. Chim. Acta, vol. 28, p. 1522 (1945) the 1945 preparation. Schenkel-Rudinö examined the Skraup reaction on a variety of 8-susbtituted quinoline derivatives in an attempt synthesize 10-HBQ. Ultimately, when sodium 8-aminonaphthalenesulphonate was heated in the presence of nitrobenzene, glycerol and 84% phosphoric acid a cyclic condensation product was generated, but not isolated. Instead, this crude mixture was subjected to oxidative conditions to aromatize the new ring system giving the product in moderate yield. Subjection of this sulfonic acid to nucleophilic substitution under NaOH/KOH melt conditions afforded, after the required aqueous work-up, 10-HBQ in 20% yield. Unfortunately, the use of the Skraup procedure to synthesize 10-HBQ is complicated given the concoction of reagents and the harsh conditions used; more significantly the conditions are not amenable to the presence of a diverse range of other functional groups.

droxyquinoline could be directed at the less favorable 7-position to afford (3) in high yields. The method of Gershon et al. (J. Org. Chem., vol. 34, p. 3268 (1969)) was used to generate compound (3) in a two-step strategy commencing with 8-hydroxyquinoline-5-sulfonic acid (1). Alkaline bromination of (1) occurs selectively at the 7-position and can be easily purified to give (2).

This bromide can then be subjected to de-sulfonation conditions to solely afford (3) in high yield. Of the two procedures, the latter method was chosen as this eliminates the possible formation of dibromo- or isomeric bromides of 8-hydroxyquinoline presenting unnecessary purification problems. With satisfactory quantities of the bromide (3), the phenolic group was readily converted to the sulfonate ester (4a). Commencing with (4a), the synthesis of 10-HBQ was achieved by completing the steps as shown in Scheme 1. Reaction of the aryne precursor (4a) with an organolithium reagent at low temperature (−78° C.) results in the formation of the intermediate 7,8-quinolyne (5). In the presence of the furan, the aryne undergoes a [4+2] cycloaddition to afford the endoxide adduct (6) in moderate yield: The material was purified by column chromatography and

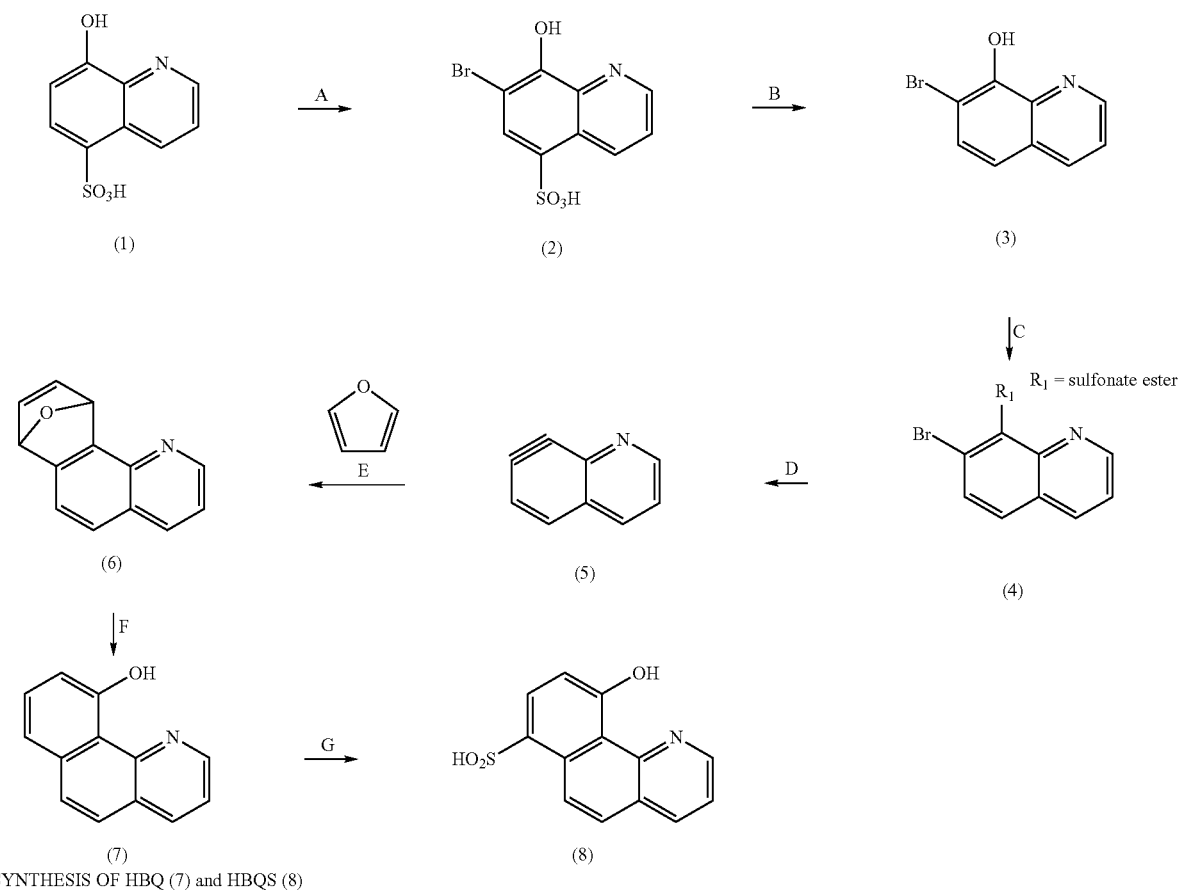

SYNTHESIS OF HBQ (7) and HBQS (8)

As an alternative procedure in mind, the precursor (1) was considered an ideal candidate for the formation of 7,8-quinolyne. Incorporation of the bromine atom at the 7-position of 8-hydroxyquinoline (3) has been reported in two different syntheses. Prior literature results had shown that at low temperatures and basic conditions, bromination of 8-hydroxyquinoline could be directed at the less favorable 7-position to afford (3) in high yields.

recrystallisation. Subjection of (6) to an excess of acid in ethanol at reflux results in the regio-selective ring opening of the endoxide to give only 10-HBQ (7a), one of two possible regio-isomers. The product obtained from this reaction is in complete spectroscopic agreement with previously available commercial 10-HBQ, material that is no longer available.

The present invention is more particularly described in the following examples that are intended as illustrative only, since numerous modifications and variations will be apparent to those skilled in the art.

All new materials have been characterized using standard spectroscopic techniques and elemental analysis. Melting points were performed and are uncorrected. All chemicals were purchased from Aldrich or Acros suppliers and used without further purification. Reactions performed in anhydrous solvents were carried out under an atmosphere of nitrogen.

EXAMPLE 1

The compound, 7-bromo-8-hydroxyquinoline-5-sulfonic acid (2), was prepared according to method of Gershon et al. (J. Org. Chem., vol. 34, p. 3208, 1969) with minor modifications. A slurry was prepared from 8-hydroxyquinoline-5-sulfonic acid monohydrate (1) (48.6 g, 0.207 mol) and potassium hydroxide (11.2 g, 5.01 mol) in water (100 mL). To this mixture was added dropwise a solution of potassium hypobromite [prepared from reaction of bromine (12.9 mL, 40.1 g, 0.25 mol, 1.2 equiv.) with a solution of potassium hydroxide (28 g, 0.50 mol) in water (120 mL)] at room temperature and left to stir for 12 hours. The crude mixture was then placed in an ice bath and 48% aqueous hydrobromic acid (about 100 mL) was added cautiously to adjust the pH to 1. The cooled product was collected by vacuum filtration. The yellow solid was washed successively with cold water (250 mL), ethanol (250 mL) and acetone (250 ml), then left to air dry for several hours (60.452 g). The proton NMR spectrum of this material showed the desired product with a trace amount of starting material. This material was dissolved in concentrated sulfuric acid (150 mL), then slowly and carefully poured into an ice cold solution of water (280 mL) and then followed by further cooling. This precipitate was filtered and washed with acetone to give fine yellow micro-crystals (55.50 g, m.p. 277 browning in color; m.p. 289° C. black and decomposed). This material was recrystallized from de-ionised water (about 3.5 L) with filtration through a glass frit to remove insoluble matter. The filtrate was cooled slowly, the precipitate collected, washed with acetone and air dried to give the bromide as fine yellow needles melting point (m.p.) 306° C., (45.0 g, 81%). $^1$H NMR (d$_6$-DMSO, 300 MHz) δ ppm 9.40 (dd, 1H, J=8.7, 1.6 Hz); 9.00 (dd, 1H, J=4.7, 1.6 Hz); 8.09 (s, 1H); 7.89 (dd, 1H, J=8.7, 4.7 Hz). $^{13}$C NMR (75.5 MHz) δ ppm 149.2, 147.1, 140.4, 136.2, 135.3, 129.7, 124.7, 122.3, 106.0.

EXAMPLE 2

The compound, 7-bromo-8-hydroxyquinoline (3), was prepared as follows. The procedure of Gershon et al. (J. Org. Chem., vol. 34, p. 3208, 1969) was followed with minor alterations. A suspension of the recrystallized bromide (8 g, 26.3 mol) in concentrated sulfuric acid (8 g) and glacial acetic (72 g) was heated at 130° C. for 7 hrs by which time all the precipitate had dissolved and the solution was a light yellow color. The solution was cooled to room temperature before pouring into a flask containing some ice and water (1000 mL). To this was added in portions KOH pellets (about 55 g) to adjust the pH to 5 by which stage a fluffy pale cream precipitate had formed. The mixture was cooled in an ice bath and the solid collected and washed with cold water (150 mL). Once air dry, the crude material was dissolved in dichloromethane, dried (MgSO$_4$) and concentrated under reduced vacuum to afford the product (3) as cream colored crystals (5.39 g, 91%). Analysis by $^1$H NMR spectroscopy indicated no impurities. Further purification was achieved by recrystallization from dichloromethane/petroleum ether to afford pure 7-bromo-8-hydroxyquinoline, m.p. 141° C., (4.84 g, 82%). $^1$H NMR (CDCl$_3$, 300 MHz) δppm 8.80 (dd, 1H, J=4.3, 1.5 Hz); 8.16 (dd, 1H, J=8.3, 1.5 Hz); 7.62 (d, 1H, J=8.8 Hz); 7.47 (dd, 1H, J=8.3, 4.3 Hz); 7.25 (d, 1H, J=8.8 Hz). $^{13}$C NMR (75.5 MHz) δ ppm 149.7, 148.6, 138.3, 136.3, 131.3, 127.4, 122.0, 118.6, 104.2.

EXAMPLE 3

Method A. A stirred solution of the bromide, 7-bromo-8-quinolinyl p-toluenesulfonate (4a), (3.00 g, 13.0 mmol, 1.1 equiv.) in ether: dichloromethane (20 mL:10 mL) and triethylamine (1.92 mL, 1.38 g, 13.0 mmol, 1.1 equiv.) cooled at 0° C. was treated dropwise with a solution of freshly recrystallized p-toluenesulphonyl chloride (2.29 g, 0.12 mol) dissolved in dry dichloromethane (35 mL). After the addition the reaction was allowed to warm to room temperature and stirred for 2 hours. The reaction mixture was diluted with dichloromethane (100 mL), filtered through a glass frit and concentrated under reduced pressure to give a pale cream solid. Analysis of this crude material by proton NMR indicated a mixture of the product and unreacted p-toluenesulphonyl chloride. This product was purified by selective recrystallization from ether/dichloromethane to give cream colored crystals (3.55 g, 78%).

EXAMPLE 4

Method B. A mixture of tetraethylammonium bromide (5.15 g, 24.5 mmol, 1.0 equiv.), 7-bromo-8-hydroxyquinoline (3) (5.50 g, 24.5 mmol) and sodium hydroxide (4.40 g, 0.11 mol, 4.5 equiv.) in water (275 mL) was stirred vigorously at room temperature until all the solids had dissolved. To this was added a solution of p-toluenesulfonyl chloride (6.71 g, 35.2 mmol, 1.4 equiv.) in dichloromethane (275 mL) which was left to stir for 28 hours. After this period the organic layer was removed and the aqueous layer extracted with dichloromethane (200 mL). The organic layers were combined, washed with water (150 mL), dried (MgSO$_4$) and concentrated under reduced pressure to afford a tan solid (9.00 g, 97%). Analysis of this material by proton NMR spectroscopy indicated that only the product was present. Recrystallization from dichloromethane/petroleum ether afforded the compound, 7-bromo-8-quinolinyl p-toluenesulfonate (4a), as pale cream colored crystals, m.p. 115° C. (8.20 g, 88%). $^1$H NMR (CDCl$_3$, 300 MHz) δ ppm 8.84 (dd, 1H, J=4.2, 1.6 Hz); 8.15 (dd, 1H, J=8.3, 1.6 Hz); 7.98–8.03 (AA' part of AA'XX', 2H); 7.71 and 7.63 (ABq, 2H, J=8.8 Hz); 7.45 (dd, 1H, J=8.3, 4.2 Hz); 7.34–7.39 (XX' part of AA'XX', 2H); 2.49 (s, 3H, CH$_3$). $^{13}$C NMR (75.5 MHz) δ ppm 151.1, 145.1, 144.7, 142.9, 135.9, 134.9, 130.8, 129.4, 128.9, 128.6, 127.2, 122.0, 118.4, 21.8.

EXAMPLE 5

7,8-quinolyne can be prepared as follows. The quinolyne (5) is a reactive intermediate that can be made in solution by stirring a solution of the tosyl ester (4a) (5.00 g, 13.2 mmol) in dry THF (150 mL) cooled at −78° C. under nitrogen and then adding n-butyllithium in hexanes (2.5 M, 5.55 mL, 13.8 mmol, 1.05 equiv.) dropwise to the solution. This leads to formation of the quinolyne that can react with a wide variety of materials including dienes. For example, the reaction with furan can yield compound 6.

EXAMPLE 6

A stirred solution of the tosyl ester (4a) (5.00 g, 13.2 mmol) in dry THF (150 mL) and freshly distilled furan (24.3 mL, 22.6 g, 0.33 mol, 25 equiv.) cooled at −78° C. under nitrogen was treated dropwise with n-butyllithium in hexanes (2.5 M, 5.55 mL, 13.8 mmol, 1.05 equiv.). The reaction was stirred for 1 hr at −78° C. and then allowed to warm to room temperature over 3 hours. The reaction mixture was treated with water (5 mL) and then heated under reduced pressure to remove most of the THF. This mixture was then diluted with water (150 mL), extracted with dichloromethane (3×100 mL). The organic layers were combined, dried (MgSO$_4$) and concentrated to give a crude brown solid (2.31 g). This material was dissolved in the minimum amount of dichloromethane/petroleum and absorbed onto a pad of neutral alumina. Gradient elution with ethyl acetate/petroleum ether afforded the product, which was recrystallized from dichloromethane/ether/petroleum ether to afford the endoxide (7,10-epoxy-7,10-dihydrobenzo[h]quinoline (6) as cream colored crystals (1.07 g, 42%). $^1$H NMR (CDCl$_3$, 300 MHz) δ ppm 8.88 (dd, 1H, J=4.1, 1.7 Hz); 8.14 (dd, 1H, J=8.4, 1.7 Hz); 7.60 and 7.57 (ABq, 2H, J=7.8 Hz); 7.27–7.33 (m, 2H); 7.21 (dd, 1H, J=5.5, 1.8 Hz); 6.54 (bs, 1H); 5.95 (m, 1H).

A solution of the endoxide (10-hydroxybenzo[h]quinoline (7)) (500 mg, 2.56 mmol) in ethanol (15 mL) and excess 37% hydrochloric acid (5.5 mL) was heated under reflux for 24 hours. The reaction mixture was cooled, diluted with ice cold water (100 mL), then stirred and slowly neutralized with solid NaHCO$_3$. The mixture was extracted with dichloromethane (3×75 mL), washed with water (75 mL), dried (Dry disk) and concentrated to give a beige colored solid (0.529 g). This crude material pre-absorbed onto silica gel and subjected to column chromatography with gradient elution with increasing portions of dichloromethane in petroleum ether and then 1% acetone in dichloromethane to give the product, 10-hydroxybenzo[h]quinoline, as a bright yellow solid (322 mg, 65%), m.p. 104° C. (literature m.p. 104–5° C., see Schenkel-Rudin et al., Helv. Chim. Acta, vol. 27, pp. 1456 (1994)). $^1$H NMR (CDCl$_3$, 300 MHz) δ ppm 4.94 (s, 1H, OH); 8.86 (dd, 1H, J=4.7, 1.7 Hz); 8.28 (dd, 1H, J=8.0, 1.7 Hz); 7.84 (d, 1H, J=8.9 Hz); 7.66 (d, 1H, J=8.9 Hz); 7.65, (t, 1H, J=7.9 Hz); 7.59 (dd, 1H, J=8.1, 4.7 Hz); 7.44 (dd, 1H, J=7.9, 1.0 Hz); 7.28 (dd, 1H, J=7.9, 1.0 Hz).

EXAMPLE 7

To a stirred solution of concentrated sulfuric acid (13 mL, 23.92 g) cooled in an ice bath was added 10-hydroxybenzo[h]quinoline (7) (4.00 g, 0.02 mol). With vigorous stirring and maintaining the temperature below 10° C. was added dropwise 20% Oleum (3 mL, 5.76 g). The reaction was gradually allowed to warm to room temperature and left stirring for 17 hours. After this period the reaction mixture was added to ice (150 g) and the fine yellow precipitate was collected and washed with acetone (6.48 g). Analysis by $^1$H NMR and COSY spectroscopy indicated the crude product to be a mixture of 10-hydroxybenzo[h]quinoline-7-sulfonic acid (A), 10-hydroxybenzo[h]quinoline-9-sulfonic acid (B) and 10-hydroxybenzo[h]quinoline-7,9-disulfonic acid (C) in the ratio of 60:16:1. The crude material was ground into a fine powder and subjected to soxhlet extraction with water. Upon completion, a fine yellow precipitate was collected from the filtrate and determined as to be a mixture of the (A) and (B) in a ratio of 2.1:1. Using proton coupling constants and COSY data, of this mixture performed in d$_6$-DMSO, the following compounds were assigned.

10-hydroxybenzo[h]quinoline-7-sulfonic acid (A): 15.41 (s, 1 H, OH); 9.01 (dd, 1H, J=4.8, 1.6 Hz); 9.00 (d, 1H, J=9.4 Hz); 8.67 (dd, 1H, J=8.1, 1.6 Hz); 8.12 (d, 1H, J=8.3 Hz); 7.94 (d, 1H, J=9.4 Hz); 7.86 (dd, 1H, J=8.1, 4.8 Hz); 7.08 (d, 1H, J=8.3 Hz).

10-hydroxybenzo[h]quinoline-9-sulfonic acid (B): 15.63 (bs, 1H, OH); 9.27–9.20 (m, 2H); 8.239 (dd, 1H, J=5.7, 8.1 Hz); 8.212 (ABq, 2H, J=9.0 Hz); 8.10 (d, 1H, J=8.3 Hz); 7.77 (d, 1H, J=8.3 Hz).

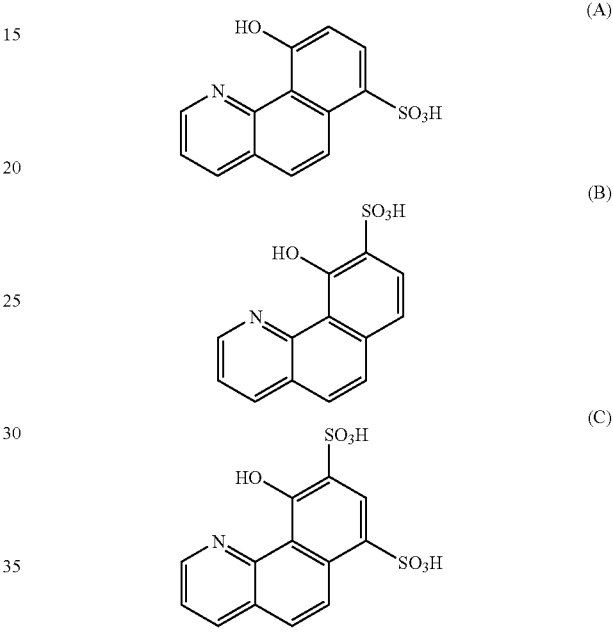

EXAMPLE 8

Reagents included: ethylenediamine tetraacetic acid (EDTA); hydroxyl benzoquinoline sulfonate (HBQS); a dissolution solution of 1% ammonium bifluoride; and, a detection solution was prepared including the following: HBQS (63.4 uM); EDTA (2.5 mM); and, lysine HCl (50.8 mM). The solution was then titrated to pH 12.6 with 10N NaOH.

Note the detection solution was made from stock solutions of 1 mM HBQS (pH approximately 12.2), 10 mM EDTA (disodium dihydrate EDTA), 100 mM lysine mono hydrochloride (pH approximately 12.6).

An Ocean Optics unit was used with the following components: USB 200 spectrometer with spectra grating #2 (UV/V is 600). The peak is near 475 nm.

The beryllium detection procedure was as follows. A Whatman #541 cellulose or a nylon membrane filter swipe (47 mm, 0.8 um pore size) was used to swipe a surface and was then folded and placed in a 15-ml polypropylene centrifuge tube. 5 ml of the dissolution solution (1% ammonium bifluoride) was added to the tube. The tube was capped and mixed or rotated on a Labquake rotator for 30 min. The solution was then filtered with a Luer-locked syringe filter (Millipore Millex-LCR PTFE, 0.45 um, 13-mm diameter or Fisher brand PTFE, 0.45 um, 25 mm diameter). Add 0.1 ml of filtrate to 1.9 ml of the detection solution in a disposable fluorescence cuvette (clear on all sides), cap, mix briefly. If any precipitate appears allow time for the precipitate to settle or filter the solution with a Luer-locked syringe filter (Millipore Millex-LCR PTFE, 0.45 um, 13-mm diameter or Fisher brand PTFE, 0.45 ☐m, 25 mm diameter) into a second cuvettte. The fluorescence spectrum was taken. Fluorescence measurements were carried out using Ocean Optic module, including a USB 2000 spectrometer, a 380-nm lamp in the LS-450 housing with attached cuvette holder. Relative irradiance measurements were carried out with a 2-sec integration time (3 averages).

Other notes on the procedure include the following. Beryllium standards were made up using beryllium ICP standards diluted into 1% ammonium bifluoride. High iron samples will initially have yellow or gold coloration; these solutions may be allowed to sit for 4 hours or more during which time the iron precipitates out and the solution clears up. Once the solution is clear there is no interference. Alternatively these solutions can be filtered and measured immediately with standard additions used to verify the detection limit. An Ocean Optics unit was used, relative irradiance mode, with calibration using an LS-1 lamp, 5-sec integration time. For high-beryllium samples, the integration time can be reduced, but standards will have to be re-run at the new integration time. The peak is near 475 nm. For samples above 30 μg per swipe a higher dilution ratio than the 1:20 is required.

The spectra measured on beryllium standards ranging from 200 parts per trillion (ppt) to 4 parts per billion (ppb) is shown in FIG. 1.

Figure 2:
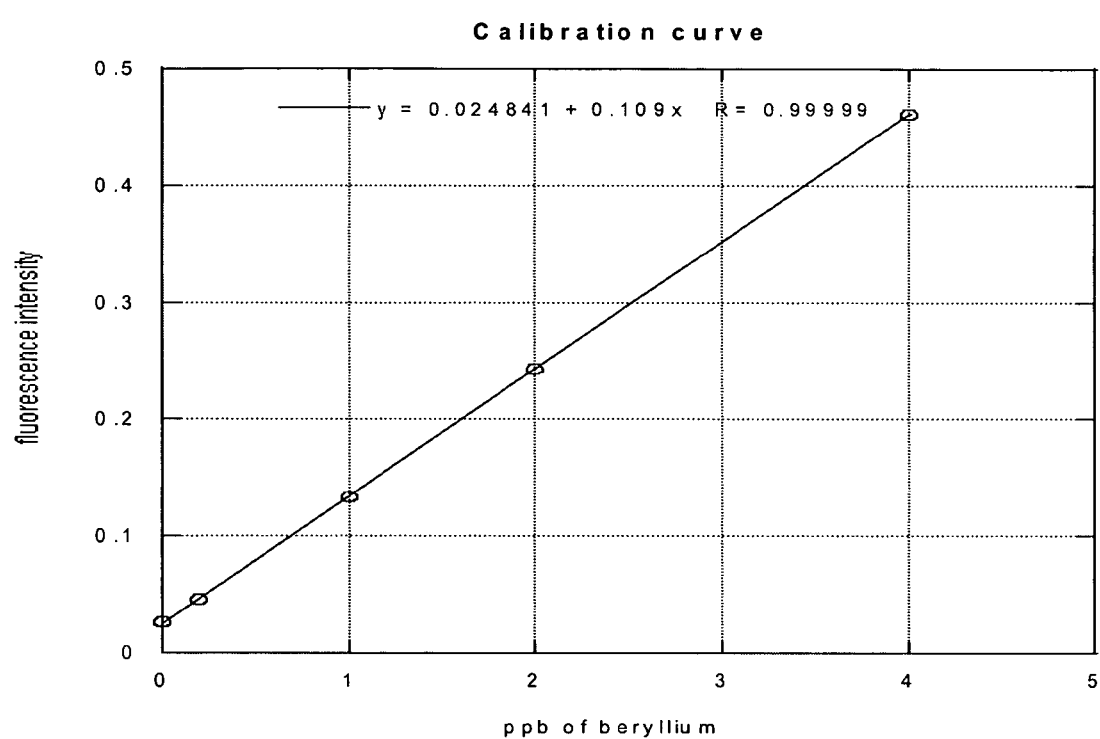
FIG. 2 shows a calibration curve plotting fluorescence intensity versus beryllium concentration in accordance with the process of the present invention.

Standards of known beryllium concentration in parts per billion (ppb) were prepared and measured according to the fluorescence procedure described above to generate the following calibration curve shown in FIG. 2.

Using the above procedure a variety of potential interfering metals were examined including aluminum, uranium, calcium, lithium, lead, zinc, iron, vanadium, tin, tungsten, copper, nickel and cobalt. It was found that even 0.4 mM of most metals did not interfere with the detection of 100 nM beryllium. In the case of iron, high concentrations may turn the solution yellow. Under this condition the sample must be allowed to settle for a few hours and then no interference is observed.

While this invention has been described as having preferred sequences, ranges, steps, materials, structures, features, and/or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the appended claims.

What is claimed is:

1. A method of determining the presence and amount of beryllium or a beryllium compound in a sample, comprising:
    admixing a sample suspected of containing beryllium or a beryllium compound with a dissolution solution for sufficient time whereby beryllium or a beryllium compound within said sample is dissolved;
    mixing a portion from said admixture with a buffered solution containing a fluorescent indicator capable of binding beryllium or a beryllium compound to the fluorescent indicator; and,
    determining the presence or amount of beryllium or a beryllium compound within said sample by measuring fluorescence from said fluorescent indicator.

2. The method of claim 1, wherein the dissolution solution is an ammonium bifluoride solution.

3. The method of claim 1, wherein the fluorescent indicator forms a six-member ring with beryllium or a beryllium compound.

4. The method of claim 1, wherein the fluorescent indicator is 10-hydroxybenzo[h]quinoline-7-sulfonate.

5. The method of claim 1, wherein the buffered solution includes a metal chelating agent.

6. The method of claim 5, wherein the metal chelating agent is EDTA or a salt of EDTA.

7. A method of determining the presence and amount of beryllium or a beryllium compound in a sample, comprising:
    admixing a sample suspected of containing beryllium or a beryllium compound with a dissolution solution for sufficient time whereby beryllium or a beryllium compound within said sample is dissolved;
    mixing a portion from said admixture with a buffered solution containing (a) a fluorescent indicator of 10-hydroxybenzo[h]quinoline-7-sulfonate capable of binding beryllium or a beryllium compound to the fluorescent indicator and (b) lysine; and,
    determining the presence or amount of beryllium or a beryllium compound within said sample by measuring fluorescence from said fluorescent indicator.

8. A method of determining the presence and amount of beryllium or a beryllium compound in a sample, comprising:
    admixing a sample suspected of containing beryllium or a beryllium compound with a dissolution solution for sufficient time whereby beryllium or a beryllium compound within said sample is dissolved;
    mixing a portion from said admixture with a buffered solution containing (a) a fluorescent indicator of 10-hydroxybenzo[h]quinoline-7-sulfonate capable of binding beryllium or a beryllium compound to the fluorescent indicator, (b) a metal chelating agent and (c) lysine; and,
    determining the presence or amount of beryllium or a beryllium compound within said sample by measuring fluorescence from said fluorescent indicator.

9. A composition of matter comprising an aqueous solution including 10-hydroxybenzo[h]quinoline-7-sulfonate and an amino acid buffer with a $pK_a$ between 7 and 13.5.

10. The composition of matter of claim 9 further comprising a metal chelating agent.

11. The composition of matter of claim 10 wherein the metal chelating agent is EDTA or a salt of EDTA.

12. A composition of matter comprising an aqueous solution including 10-hydroxybenzo[h]quinoline-7-sulfonate and an amine buffer with a $pK_a$ between 7 and 13.5 wherein said amine buffer is lysine.

13. A composition of matter comprising an aqueous solution including 10-hydroxybenzo[h]quinoline-7-sulfonate, a metal chelating agent and an amine buffer with a $pK_a$ between 7 and 13.5 wherein said amine buffer is lysine.

* * * * *